United States Patent [19]
Dennis

[11] Patent Number: 5,727,770
[45] Date of Patent: Mar. 17, 1998

[54] DOUBLE VALVE CANNULA SEAL

[75] Inventor: William G. Dennis, Jacksonville, Fla.

[73] Assignee: Core Dynamics, Inc., Jacksonville, Fla.

[21] Appl. No.: 796,193

[22] Filed: Feb. 7, 1997

[51] Int. Cl.$^6$ ............................................. F16L 37/28
[52] U.S. Cl. ..................... 251/149.1; 604/256; 604/905
[58] Field of Search ............................ 604/256, 905; 251/149.1

[56] References Cited

U.S. PATENT DOCUMENTS

| | | | |
|---|---|---|---|
| 4,909,798 | 3/1990 | Fleischhacker et al. | 251/149.1 |
| 4,946,133 | 8/1990 | Johnson et al. | 251/149.1 |
| 5,092,857 | 3/1992 | Fleischhacker | 251/149.1 |
| 5,456,284 | 10/1995 | Ryan et al. | 604/656 |

*Primary Examiner*—A. Michael Chambers
*Attorney, Agent, or Firm*—Thomas C. Saitta

[57] ABSTRACT

A double valve seal to prevent escape of liquids or gases through a cannula, the seal having a diaphragm valve with a circular aperture to seal the cannula when an instrument is inserted and a spilt conical valve to seal the cannula when no instrument is present. A pair of diametrically opposed ribs are positioned beneath the end member and are aligned with the split in the conical valve so as to abut the open end of the cannula and act as pivot points to impart compressive force against the two halves of the conical valve to improve the effectiveness of the seal.

15 Claims, 4 Drawing Sheets

DOUBLE VALVE CANNULA SEAL

BACKGROUND OF THE INVENTION

This invention relates generally to elastomeric seals or valves used to seal a cannula to prevent escape of liquids or gases from the cannula while allowing for insertion and removal of instruments. More particularly, the invention relates to such seals which are designed as caps to cover the open proximal end of the cannula. Even more particularly, the invention relates to such seals which have a double sealing mechanism—one valve which seals the cannula when an instrument is present in the cannula and another valve which seals the cannula when no instrument is present.

A cannula is a hollow tube-like device which is used to maintain an open passageway through the skin and other subcutaneous layers into an internal cavity of a patient undergoing medical treatment or procedures. The cannula is typically combined with puncturing means such as a trocar or needle retained within the cannula, the needle or trocar being removed after the combination has been inserted through the outer layers, thereby leaving the cannula to maintain the opening and allow for insertion of various instruments. Because the cannula interior is an open passageway when no instrument is inserted, it is necessary to seal the cannula to prevent loss of bodily fluids, gases or other liquids. At the same time, it is also desirable to have a sealing mechanism which prevents such losses when instruments are present in the cannula.

The simplest solution for sealing the cannula when an instrument is in place is to provide a flexible diaphragm valve made of an elastomeric material, the valve having a circular aperture sized slightly smaller than the external diameter of the inserted instrument. This type of valve seal, however, does not prevent losses of liquid or gas when the instrument is removed. To improve on this design, it is known to provide cannula sealing devices with self-closing valves, such as shown in U.S. Pat. No. 5,269,763 issued to Boehmer et al. This type of valve, known as a duckbill valve, remains in the closed position unless an instrument is inserted therethrough. When the instrument is removed, the design of the valve and internal pressure from the body cavity cause it to close to seal the cannula. A problem encountered with this design is that the valve does not provide a tight seal when the instrument is in place, since the instrument is circular in cross-section but the valve is a combination of intersecting lines which create right angle corners at the distal valve opening. When these corners are forced apart to allow passage of the instrument, they do not create a circumferential seal about the cylindrical instrument. Another problem is that the valve may not form a complete seal after repeated insertions and removal of instruments in the cannula.

To address the problem of gas or liquid escape from the cannula when an instrument is inserted, another seal design is known which comprises a pair of seals or valves, as shown by U.S. Pat. No. 4,655,752 to Honkanen et al. In this design, one valve member acts to seal the cannula when no instrument is inserted and a second valve member seals the cannula when an instrument is in place. The combination shown in Honkanen et al. is a generally conical member split into symmetrical quarters by a pair of slits plus a generally conical member truncated to form a circular aperture. With an instrument in place, the split conical valve is pushed apart by the instrument and the circular aperture valve circumferentially abuts the cylindrical instrument to seal the cannula. When the instrument is removed, the circular aperture valve has no function while the split conical valve is closed by a combination of the elastic memory inherent in the structure and the back-flow pressure of gases or liquids within the cannula. Particular problems with the Honkanen et al. design are that it must be constructed of two separate members, the split conical valve tends not to close completely when the instrument is withdrawn, and the wall thickness of the circular aperture valve near the opening is difficult to properly size since it must meet the divergent objectives of simultaneously providing enough rigidity to allow removal of the instrument without distorting or harming the valve while allowing the wall thickness at the aperture to be thin enough to provide an efficient seal.

It is an object of this invention to provide a cannula sealing device formed of an elastomeric material which allows for insertion and removal of various instruments into the interior of the cannula and which completely seals the cannula to prevent loss of either gas or liquid both when an instrument is present and when the instrument is removed. It is a further object to provide such a device which utilizes two independent valve seals, one of which seals the cannula when the instrument is in place and the other of which seals the cannula when the instrument is removed. It is a further object to provide such a device where the valve sealing the cannula when an instrument is inserted is a diaphragm-type valve having a circular aperture and where the valve sealing the cannula when no instrument is present comprises a generally conical member having a single slit to create two symmetrical halves, where the conical halves are compressively biased together by a set of biasing ribs positioned at the base of the conical member and aligned along the plane of the slit to better seal the two halves.

SUMMARY OF THE INVENTION

The invention is in general an elastomeric double valve sealing device for a cannula which allows for insertion and removal of instruments into the core of the cannula and which seals the cannula against loss of liquid or gas when the instrument is in place as well as when the instrument is removed. The invention preferably is formed as a cap positioned on the proximal end of a cannula, but may comprise a cannula seal contained within separate retention members of the cannula or the combination of the cap seal and cannula. The seal comprises a pair of valves, one being configured as a diaphragm-type valve having a circular central opening mounted in a generally planar, relatively thin in cross-section, end member aligned perpendicularly to the longitudinal axis of the seal and the cannula. The other valve is configured as a generally conical member divided into two symmetrical halves by a slit, the slit occupying a plane which contains the axis. The first valve seals the cannula when an instrument is inserted, the latter valve seals the cannula when no instrument is present.

The split conical valve extends from the interior side of the end member in the distal direction, and the end member extends radially outward beyond the base of the conical valve. A pair of diametrically opposed biasing ribs extend radially outward from the base of the conical valve on the interior side of the end member such that each of the biasing ribs extend across the annular open end of the cannula to the sleeve member, which fits down over the exterior of the cannula to secure the sealing device in place as a cap. The biasing ribs are raised members, preferably semi-circular in cross-section, but may also be configured as rectangular, square, triangular, etc. If the seal is maintained in place by separate cannula members, the sleeve need not be present. The biasing ribs are aligned along the plane of the slit which bisects the conical valve. In the preferred embodiment, the sleeve is provided with plural annular seating flanges to better secure the seal device onto the cannula, and in the most preferred embodiment the cannula is provided with corresponding annular channels to receive the seating flanges. When the seal device is secured onto the end of the cannula, the biasing ribs raise opposing circumferential segments of the end member while the remaining circumferential portions of the end member are pulled tightly against the end of the cannula. This imparts a compressive force on the split halves of the conical valve perpendicular to the plane of the slit, such that the two halves are pressed together with a force greater than the compressive force resulting from elastic memory.

In the preferred embodiment, the double valve cannula seal comprises an integral member such that the two valves and all other components are formed of a single elastomeric component. It is also preferred that the diaphragm-type valve be thinner in cross-section than the remainder of the end member such that a better seal will be achieved around the inserted instrument.

DETAILED DESCRIPTION OF THE INVENTION

With reference to the drawings, the invention will now be described in detail with due regard for the preferred embodiment and best mode. In the description, the term proximal shall be taken as referencing the external end of the cannula or the direction toward same, and the term distal shall be taken as referencing the interior end of the cannula which is inserted into the skin or the direction toward same.

In general, the invention is a double valve cannula seal, or the cannula and cannula seal combination, preferably embodied as a cap applied to the open proximal end of the cannula. The cannula seal is composed of an elastomeric material which is deformable and resilient, such that the seal maintains a definitive structure at rest but can be flexed and stretched, and where the material has a memory such that the seal seeks to return to its at rest form when compressive or tensile forces applied to the device are removed or reduced. The elasticity of the material should be sufficient to allow the valves to form tight seals with the cannula, with instruments inserted in the cannula and with separate components of the seal itself. Such materials are well known in the art.

Figure 1:
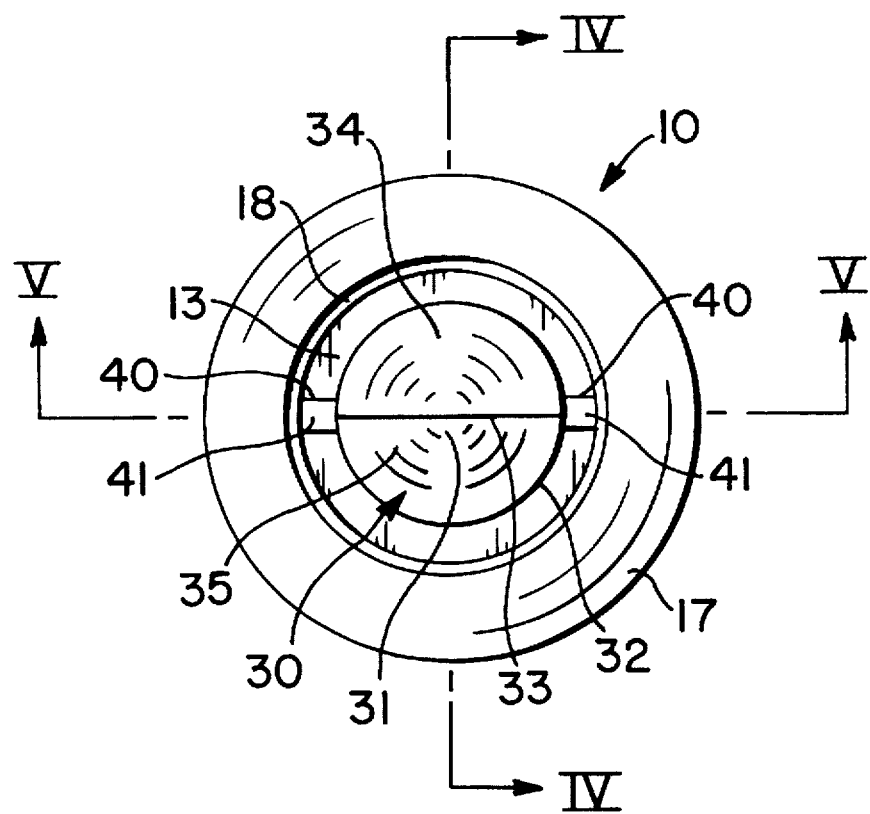
FIG. 1 is distal view of the invention.
Figure 2:
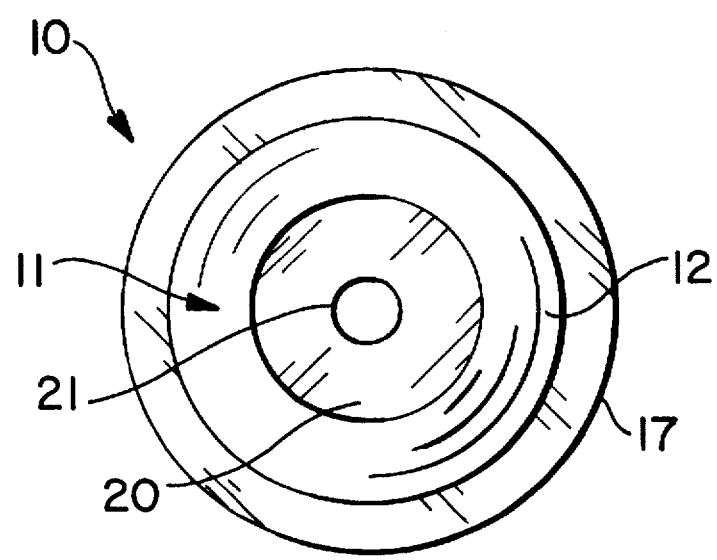
FIG. 2 is a proximal view of the invention.
Figure 3:
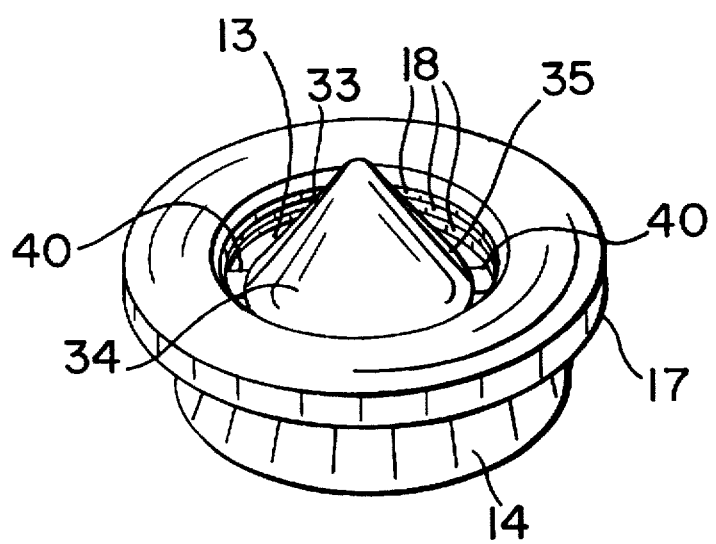
FIG. 3 is a perspective view of the distal end of the invention.
Figure 4:
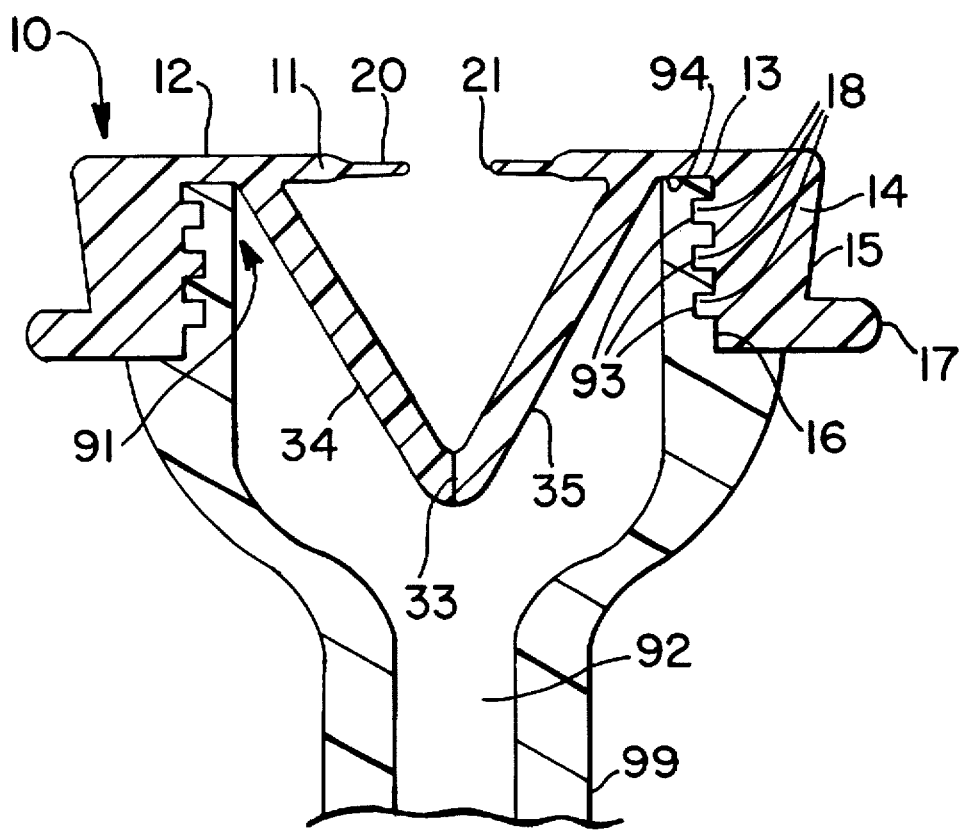
FIG. 4 is a cross-sectional view showing the sealing cap in position on a cannula, taken along line IV—IV of FIG. 1.
Figure 5:
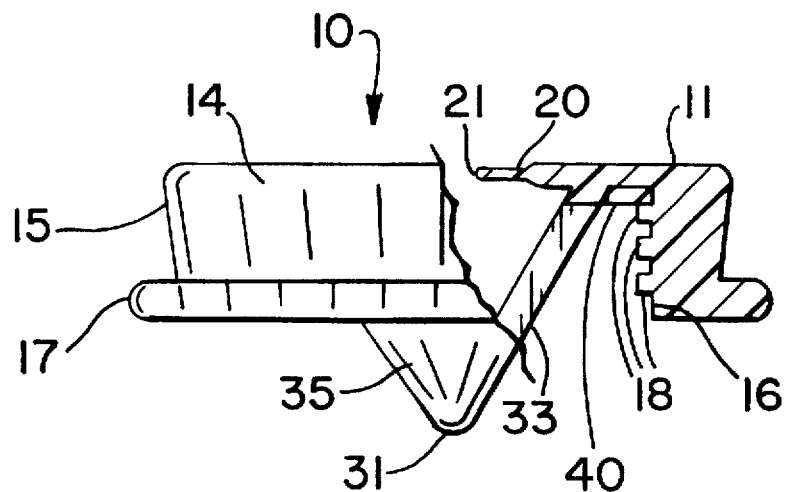
FIG. 5 is a partially exposed side view, with the exposed portion in cross-section taken along line V—V of FIG. 1.
Figure 6:
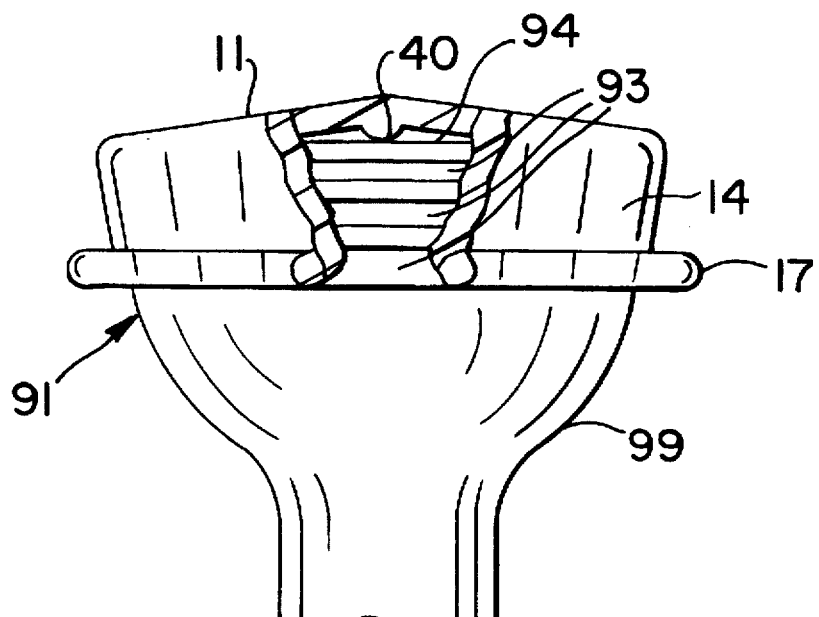
FIG. 6 is a partially exposed side view of the invention showing the biasing influence of a biasing rib on the end member.
Figure 7:
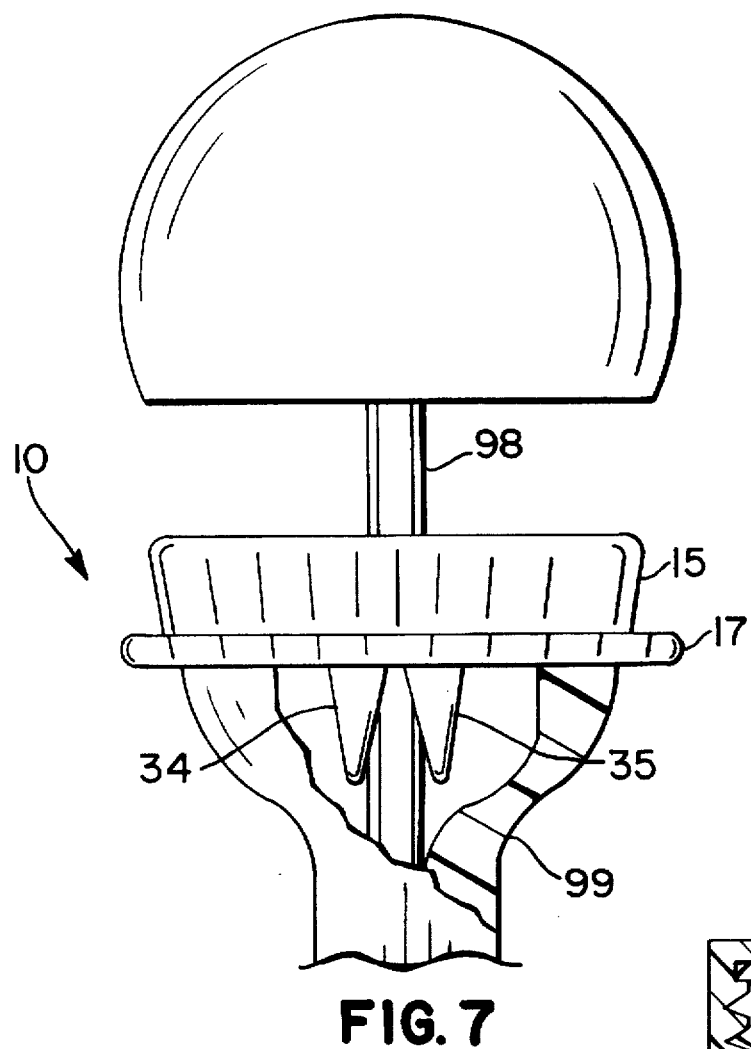
FIG. 7 is a partially exposed view showing the positioning of the cone halves when an instrument is inserted in the cannula.

As shown in FIGS. 1-3, the double valve cannula seal 10 generally comprises an annular sleeve member 14 closed by an end member 11 having a generally planar exterior side 12, with a diaphragm valve 20 centrally positioned on the end member 11 and a generally conical split valve 30 connected on the interior or distal side 13 of the end member 11. The seal 10 is configured to releasably affix to the proximal open end 91 of a cannula 99 having a longitudinally extended core 92 to receive a trocar or other instrument 98 having a cylindrical body, as shown in FIGS. 6–7. Sleeve 14 extends a short distance in the distal direction from end member 11 and stretches to encircle the exterior of the cannula 99 adjacent the open proximal end 91, the combination of the annular sleeve 14 and generally planar end member 11 acting to close the open end 91 except for the opening 21 of diaphragm valve 20, as shown in FIGS. 4–5. Preferably, the exterior wall 15 of sleeve member 14 is provided with an exterior annular flange 17 which provides a gripping member for easier application and removal of the seal 10 from the cannula 99. Also preferably, the interior wall 16 of sleeve member 14 is provide with one or more inwardly extending annular seating flanges 18 and the exterior of the cannula 99 is provided with corresponding seating channels 93 to receive the seating flanges 18, the mechanical interlocking of these elements providing for improved retention of the seal 10 on the cannula 99. The interior or distal side 13 of end member 11 generally abuts the annular abutment surface 94 or proximal cannula end 91.

The cannula core 92, proximal end 91 and sleeve 14 are annular and share a longitudinal central axis. A diaphragm valve 20 having a circular central aperture or opening 21 with its midpoint aligned on the longitudinal axis is centered on end member 11. Diaphragm valve 20 is preferably thinner in cross-section than the surrounding cross-sectional thickness of end member 11. This allows aperture 21 more flexibility to form a tighter seal with any instruments 98 inserted through the seal 10 into the cannula 99. Aperture 21 is sized smaller than the diameter of core 92, preferably about 60 percent smaller, to insure that a good seal will be obtained with any sized instrument 98 reasonably expected to be used with a given cannula 99. The thinness of diaphragm valve 20 further insures that there will be enough elasticity in the aperture 21 to conform to the maximum size instrument 98 able to be used with a given cannula 99.

Extending in the distal direction from the interior side 13 of end member 11 is a generally conical split valve 30. The base 32 of the conical valve 30 connects to the end member 11 so as to fit internally within and generally abut the interior edge of annular abutment surface 94 on the proximal cannula end 91, while the apex 31 of the conical valve 30 extends within the cannula 99 in the distal direction. The conical valve 30 comprises a first cone half 34 and a second cone half 35 created by a linear slit 33. Slit 33 extends through the apex 31 and substantially but not completely down both sides to the base 32 and occupies a plane which also includes the longitudinal axis of the core 92 and seal 10. In this manner first cone half 34 and second cone half 35 are symmetrical and equal in all respects. The conical split valve 30 is much thicker in cross-section than diaphragm valve 20, since the first and second cone halves 34 and 35 must have sufficient rigidity to maintain shape when compressed against each other when no instrument 98 is present in the cannula 99. For example, in a cannula seal 10 with end member 11 having a thickness of approximately 0.03 inches, the conical split valve may have a thickness of approximately 0.06 inches. When an instrument 98 is inserted, the two cone halves 34 and 35 are pushed apart, as shown in FIG. 7, and the cannula is sealed by diaphragm valve 20.

A pair of opposing biasing ribs 40 are positioned on the interior side 13 of end member 11 extending radially from and joining the base 32 of conical valve 30 to the interior wall 16 of sleeve 14. Each biasing rib 40 comprises a raised member, preferably having a curved surface 41, which directly abuts the annular abutment surface end 94 of proximal cannula end 91 when the seal 10 is in place on the cannula 99. The biasing ribs 40 are positioned a line which passes through the longitudinal axis and which is contained within the plane formed by slit 33, such that a biasing rib 40 is located at each endpoint of slit 33 adjacent base 32. Biasing ribs 40 act as pivots for the first and second cone halves 34 and 35, such that when sleeve 14 and end 11 are properly positioned on cannula 99, the circumferential portion of end member 11 is differentially or non-uniformly flexed. This occurs because the circumferential regions between and not adjacent to the biasing ribs 40 are drawn relatively tightly against annular abutment surface 94 so that there is actual contact between the interior side 13 of end member 11, while the biasing ribs 40 prevent contact between the interior side 13 of the circumferential region of end member 11 located at and immediately adjacent each biasing rib 40 and maintain this region in a raised configuration, as seen in FIG. 6. This configuration flexes end member 13 and imparts compressive forces perpendicular to the plane of slit 33 which push each of cone halves 34 and 35 together with greater force than would be present merely from the combination of elastic memory properties of the material and force from internal gases or liquids. This insures that the two cone halves 34 and 35 will remain tightly sealed when the instrument 98 is removed from the cannula, even after repeated insertions and removals.

Figure 8:
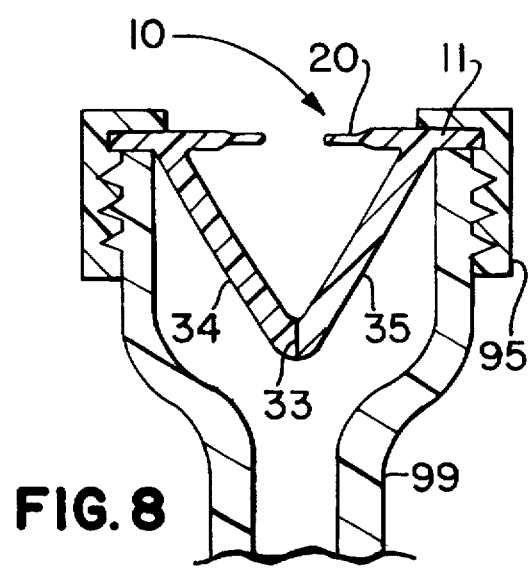
FIG. 8 is a cross-sectional view similar to FIG. 4, showing an alternative embodiment of the invention.

An alternative embodiment is shown in FIG. 8, where the seal 10 has no sleeve member 14. The double valve seal 10 is retained in place on cannula 99 by the provision of a separate retaining member 95 attachable to the cannula 99, such as by threaded portions as shown. The end member 13 is compressed between the cannula 99 and retaining member 95, with operation the same as set forth above.

It is contemplated that equivalents and substitutions for components set forth above may be obvious to those skilled in the art, and the true scope and definition of the invention therefore is to be as set forth in the following claims.

I claim:

1. A seal for an instrument receiving cannula, the seal having a longitudinal axis and comprising a diaphragm valve mounted in an end member, a generally conical split valve extending from said end member, and a pair of opposing biasing ribs mounted on said end member, said diaphragm valve having a circular aperture to sealingly receive an instrument inserted through said diaphragm valve and into said cannula, said conical split valve being divided by a linear slit into a first cone half and a second cone half, said linear slit passing through said longitudinal axis to define a plane, said biasing ribs being positioned on a line passing through said longitudinal axis and contained within said plane and adjacent said slit whereby said ribs abut said cannula and impart a compressive force to said first cone half and said second cone half to sealingly close said conical split valve when no instrument is inserted through said conical split valve.

2. The seal of claim 1, further comprising a sleeve member connected to said end member, said sleeve member receiving said cannula and connecting said seal to said cannula.

3. The seal of claim 2, where said sleeve member pulls said end member against said cannula whereby a circumferential portion of said end member not adjacent said biasing ribs abuts said cannula.

4. The seal of claim 1, where said seal is formed of an elastomeric material.

5. The seal of claim 1, where said conical split valve further comprises a base adjacent said end member and an apex, and where said slit passes through said apex and ends on opposite sides of said conical split valve adjacent said base.

6. The seal of claim 1, where said cannula has an open proximal end and said end member and said biasing ribs abut said open proximal end.

7. The seal of claim 1, where said sleeve member comprises an exterior side and an interior side, and further comprises annular seating flanges mounted on said interior side to improve retention of said seal on said cannula.

8. The seal of claim 7, where said sleeve member further comprises an annular flange mounted on said exterior side.

9. The seal of claim 1, where said biasing ribs are semicircular in cross-section.

10. A combination cannula and seal for receiving instruments, said cannula comprising an open proximal end with an annular abutment end surface, a core for receiving instruments and a longitudinal axis, said seal being mounted on said proximal end of said cannula and comprising an end member having an interior side and a circumferential portion, a diaphragm valve comprising a circular aperture mounted on said end member, said circular aperture having a midpoint on said longitudinal axis, a generally conical split valve extending from said end member into the interior of said cannula, said conical split valve comprising a linear slit defining a first cone half and a second cone half, said slit occupying a plane which contains said longitudinal axis, and a pair of diametrically opposing biasing ribs mounted on said interior side of said end member adjacent said slit on a line passing through said longitudinal axis and contained within said plane, said biasing ribs abutting said annular abutment end surface of said open proximal end of said cannula, where portions of said circumferential portion of said end member not adjacent said biasing ribs are drawn against said annular abutment end surface of said open proximal end of said cannula, such that said first cone half and said second cone half pivot against said biasing ribs and compressive force is imparted to sealingly close said slit.

11. The combination cannula and seal of claim 10, said seal further comprising a sleeve member connected to said end member, said sleeve member receiving said proximal end of said cannula.

12. The combination cannula and seal of claim 11, where said cannula further comprises annular seating channels and said sleeve member further comprises annular seating flanges, said seating flanges corresponding to and received by said seating channels.

13. The combination cannula and seal of claim 10, where said cannula further comprises a retaining member attached to said cannula, where said seal is retained between said retaining member and said cannula.

14. The combination cannula and seal of claim 10, where said conical split valve comprises a base connected to said end member and an apex, and where said slit passes through said apex and ends adjacent said base.

15. The combination cannula and seal of claim 10, where said biasing ribs are semicircular in cross-section.

* * * * *